(12) United States Patent
Foley (10) Patent No.: US 6,875,198 B2
(45) Date of Patent: Apr. 5, 2005

(54) SURGICAL SUCTION REGULATOR VALVE

(76) Inventor: Kevin T. Foley, 2877 Keasler Cir., Germantown, TN (US) 38139

( * ) Notice: Subject to any disclaimer, the term of this patent is extended or adjusted under 35 U.S.C. 154(b) by 20 days.

(21) Appl. No.: 10/287,546

(22) Filed: Nov. 5, 2002

(65) Prior Publication Data

US 2003/0216690 A1 Nov. 20, 2003

Related U.S. Application Data

(60) Provisional application No. 60/380,304, filed on May 15, 2002.

(51) Int. Cl.[7] ............................................... A61M 1/00
(52) U.S. Cl. ...................... 604/119; 604/118; 604/902; 604/249; 251/347; 251/318
(58) Field of Search ............................ 604/30, 33, 35, 604/36, 45, 246, 249, 537, 902, 118, 119, 313, 316; 251/347, 318–325

(56) References Cited

U.S. PATENT DOCUMENTS

| 3,395,705 | A | | 8/1968 | Hamilton |
| 3,625,221 | A | * | 12/1971 | Corbett ........................ 604/119 |
| 3,834,388 | A | | 9/1974 | Sauer |
| 3,863,635 | A | * | 2/1975 | Swatman ..................... 604/119 |
| 4,662,871 | A | | 5/1987 | Rafelson |
| 4,784,649 | A | * | 11/1988 | Imonti et al. ................ 604/240 |
| 4,878,900 | A | | 11/1989 | Sundt |
| 4,961,245 | A | * | 10/1990 | Barnes et al. .................. 15/339 |
| 4,964,849 | A | * | 10/1990 | Robicsek ..................... 604/35 |
| 5,127,694 | A | * | 7/1992 | Oehninger ................. 294/64.1 |
| 5,169,192 | A | * | 12/1992 | Allison et al. ............. 294/64.1 |
| 5,203,769 | A | * | 4/1993 | Clement et al. ............... 604/32 |
| 5,320,328 | A | | 6/1994 | Decloux et al. |
| 5,531,712 | A | | 7/1996 | Malcolm et al. |
| 5,571,081 | A | * | 11/1996 | Adhoute ..................... 604/6.07 |
| 5,676,136 | A | * | 10/1997 | Russo ..................... 128/205.24 |
| 5,730,727 | A | * | 3/1998 | Russo .......................... 604/118 |
| 5,836,909 | A | * | 11/1998 | Cosmescu ..................... 604/35 |
| 5,890,516 | A | * | 4/1999 | Talamonti ................... 137/605 |
| 5,899,884 | A | | 5/1999 | Cover et al. |
| 5,919,174 | A | | 7/1999 | Hanson |
| D412,984 | S | | 8/1999 | Cover et al. |
| 5,993,410 | A | * | 11/1999 | Vincent et al. ............... 604/27 |
| 6,343,823 | B1 | * | 2/2002 | Busby ........................ 294/64.1 |
| 6,364,853 | B1 | * | 4/2002 | French et al. ................. 604/35 |

* cited by examiner

Primary Examiner—Cris L. Rodriguez
(74) Attorney, Agent, or Firm—Nixon & Vanderhye, P.C.; Frank P. Presta (57) ABSTRACT

A suction regulator valve adapted to be installed between a suction pump or other vacuum source and a suction tube or catheter, the valve comprising a hollow valve body having an outer surface with a generally transverse or circumferential opening therethrough, and a valve member slidably mounted on the valve body for generally transverse or circumferential movement thereon. The valve member is movable between an open position wherein the opening is uncovered and a closed position wherein the valve member covers and closes the opening. The valve member is positioned for engagement by the thumb or other finger of a user to enable the movement of the valve member to cover or uncover all or a portion of the opening. The suction regulator valve may be a separate member, may have a handle portion or may be formed integrally with a suction wand or other suction device.

17 Claims, 9 Drawing Sheets

SURGICAL SUCTION REGULATOR VALVE

CROSS REFERENCE TO RELATED APPLICATIONS

The present application includes the subject matter and claims the priority of Provisional Patent Application Ser. No. 60/380,304 filed on May 15, 2002 and entitled "Surgical Suction Regulator Valve".

FIELD OF INVENTION

The present invention relates generally to a regulator valve and, more particularly, to a surgical suction regulator valve that can be installed in series between a suction tube and a vacuum source.

BACKGROUND OF THE INVENTION

During the course of a surgical operation on a patient, it is often necessary to remove from the site of the operation various body fluids, including blood, which tend to collect there. During childbirth, it is often necessary to remove meconium from the newborn using an intrapartum nasopharyngel suction device. In either case, the suction probe or catheter is usually connected to a pump or other type of vacuum source by means of a flexible tube. It has been found convenient to install a relief valve between the suction probe and the pump in order to control the amount of vacuum applied to the probe. Such a suction control usually consists of a valve which can be adjusted to admit a certain flow of ambient air into the tube, thus, reducing the suction force at the probe.

In some suction devices, the air intake of the regulating valve is controlled by the operators positioning a finger over the air-intake as disclosed in U.S. Pat. No. 5,000,175, Pue. Such a device must be continuously handled by the operator. Moreover, should the operator drop the device, the maximum rate of ambient air is admitted, thus reducing or completely interrupting the suction.

Other medical suction control devices, such as the one disclosed in U.S. Pat. No. 4,356,823, Jackson, offer only a limited range of vacuum adjustments and no way to adjustably stabilize the setting of the air-intake.

Similar suction control devices in the prior art have been difficult or inconvenient to operate while being gripped with one hand. Also, they may be subject to inadvertent adjustment when tension is applied to the suction tubing.

SUMMARY OF THE INVENTION

A principal object of the present invention is to provide a simple, yet practical regulator valve, to be placed in series between a surgical suction catheter and a surgical suction pump or other type of vacuum source, that can be easily and accurately adjusted, and can maintain its setting unattended. It is also an object of the present invention that the suction regulator valve be operable with one hand, be so simple and inexpensive that it can be disposed of after a single use, and be made of a material that can be conveniently sterilized with gamma rays.

These and other objects are achieved by the suction regulator valve of the present invention wherein the valve body comprises a generally transverse or circumferential opening in communication with the hollow interior thereof, and a valve member is slidably or rotatably mounted on the outer surface of the valve body for transverse or circumferential movement thereon between an open position wherein the opening is uncovered and a closed position wherein it covers the opening. The valve member may be easily and accurately manipulated by the thumb or other finger of the user while gripping the suction regulator valve with one hand. The suction regulator valve may be a separate member, may have a handle portion or may be assembled as part of a suction wand or other suction device.

DESCRIPTION OF THE PREFERRED EMBODIMENTS

Figure 1:
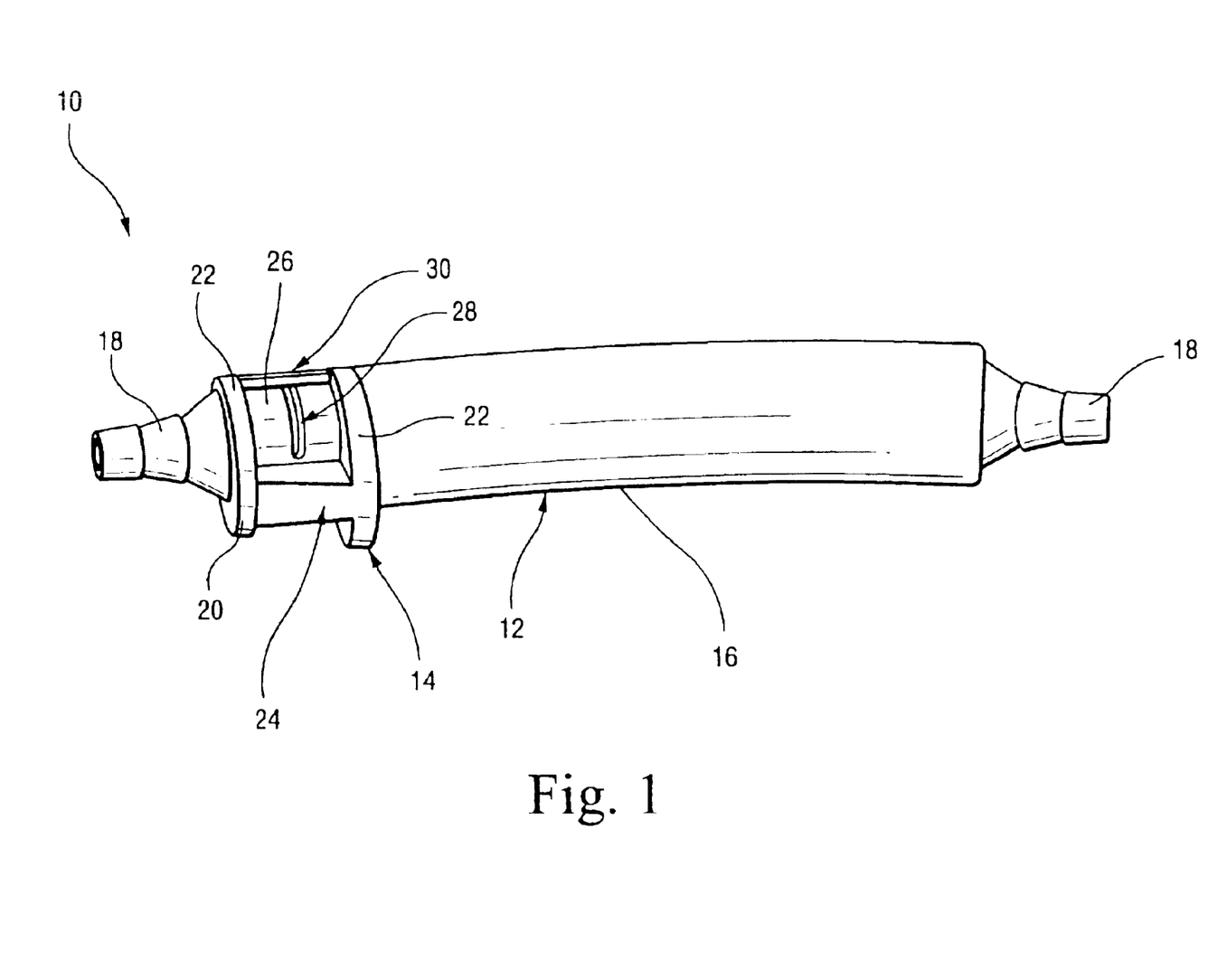
FIG. 1 is a perspective view of one side portion of the suction regulator valve of the present invention.
Figure 1A:
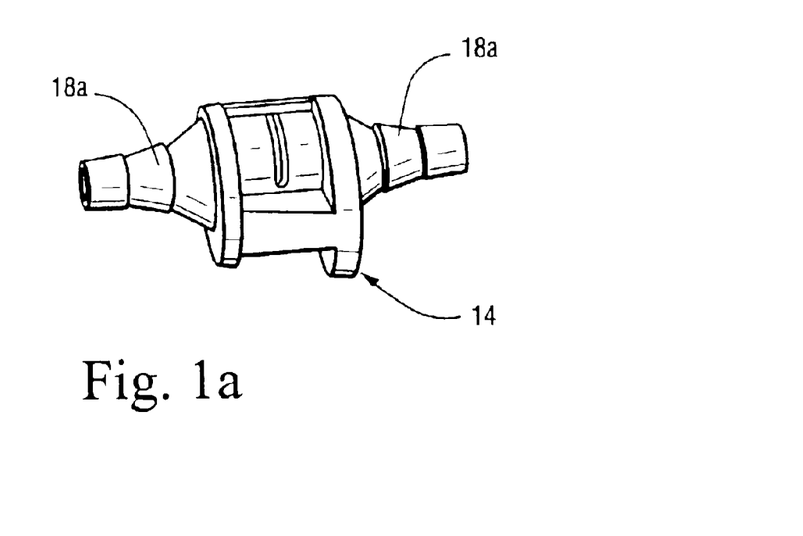
FIG. 1a is a perspective view of the suction regulator valve of FIG. 1 without the handle portion.

Referring to FIG. 1, the regulator valve 10 of the present invention preferably is formed of a medically suitable thermal plastic or other suitable material, and generally comprises a hollow body 12 having a valve portion 14 and a hollow handle portion 16 with tapered, stepped end portions 18 or the like that are adapted to be attached to suction tubing (not shown). The handle portion 16 may be slightly curved to enable it to fit easily in the palm of a physician or other user. Alternatively, the handle portion 16 may be omitted and the valve portion 14 may be provided with the tapered, stepped end portions 18a on both ends thereof, as shown in FIG. 1a.

As shown in FIGS. 1–5, the valve portion 14 comprises a hollow valve body 20 which may be of a generally cylindrical configuration with a generally circular or elliptical cross section having end walls 22 defining a recessed area and a stop 24 extending longitudinally or axially between the end walls 22. The recessed outer surface 26 of the valve body 20 between the end walls 22 comprises a generally transverse or circumferential opening 28 of any suitable shape (FIGS. 1, 4 and 6) in communication with the hollow interior of the valve portion 14.

Figure 2:
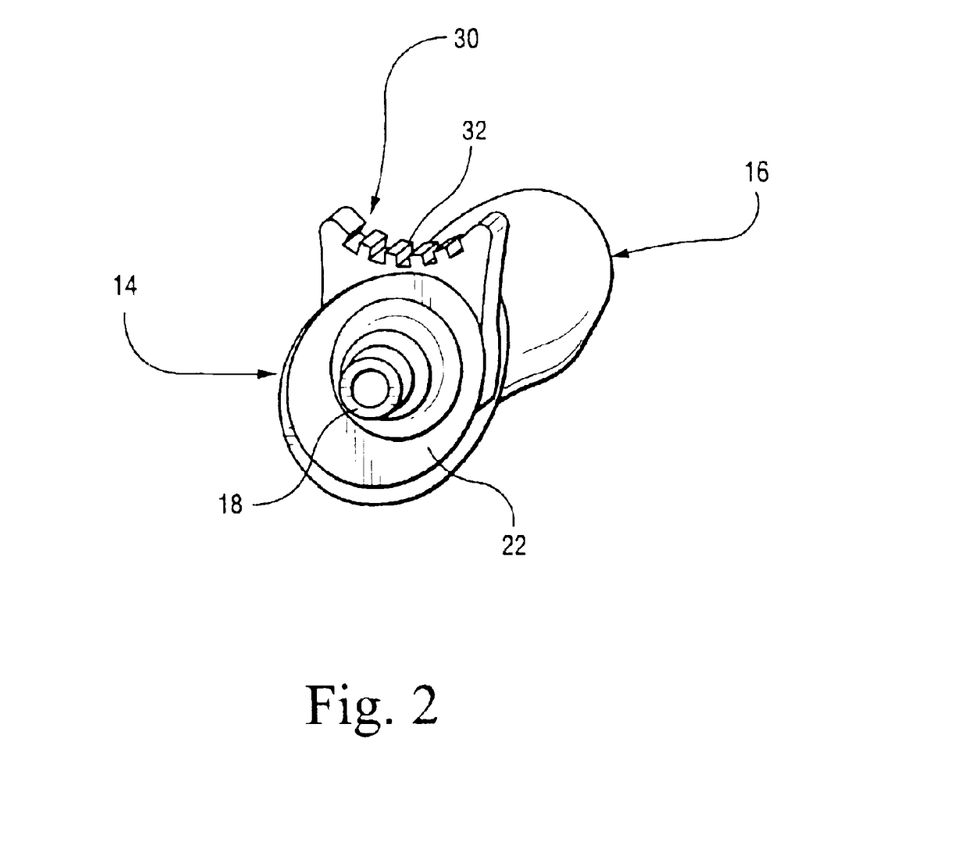
FIG. 2 is a perspective view of one end of the suction regulator valve.
Figure 3:
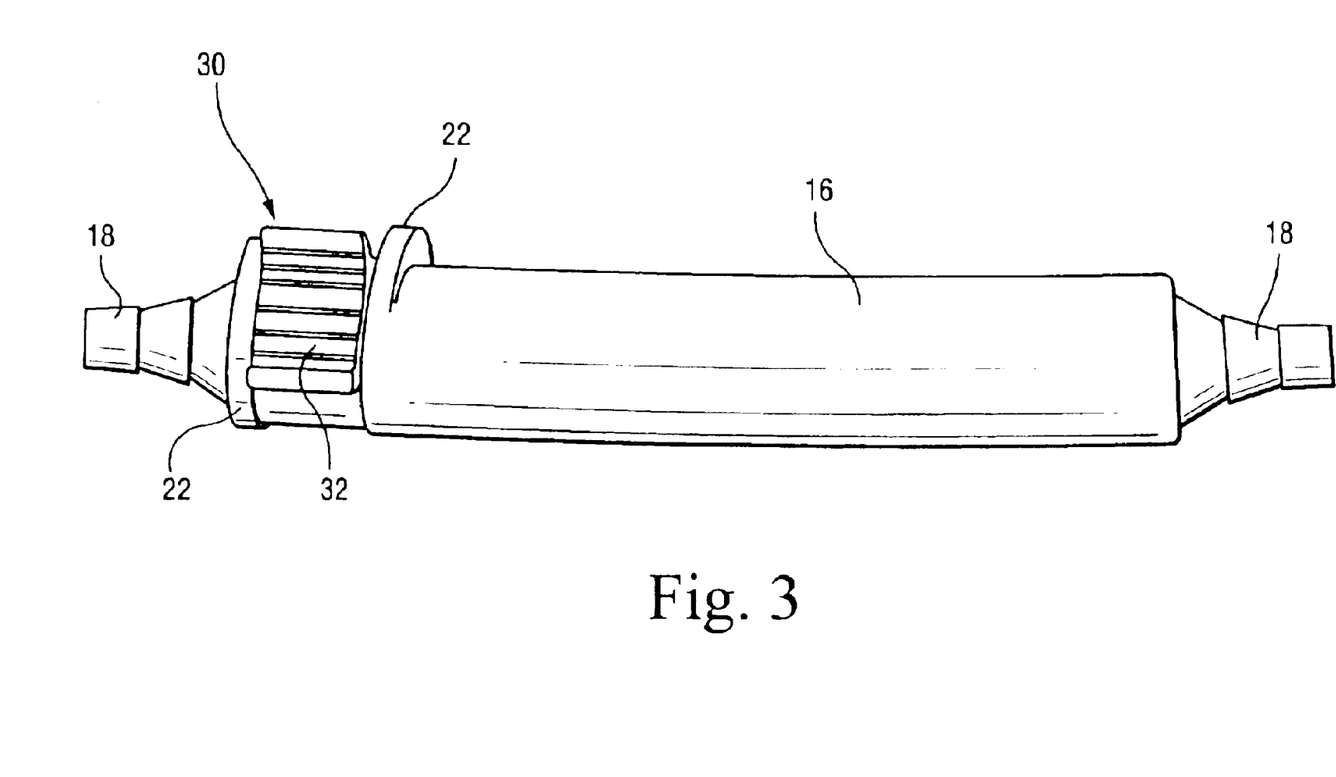
FIG. 3 is a perspective view of another side portion of the suction regulator valve.
Figure 4:
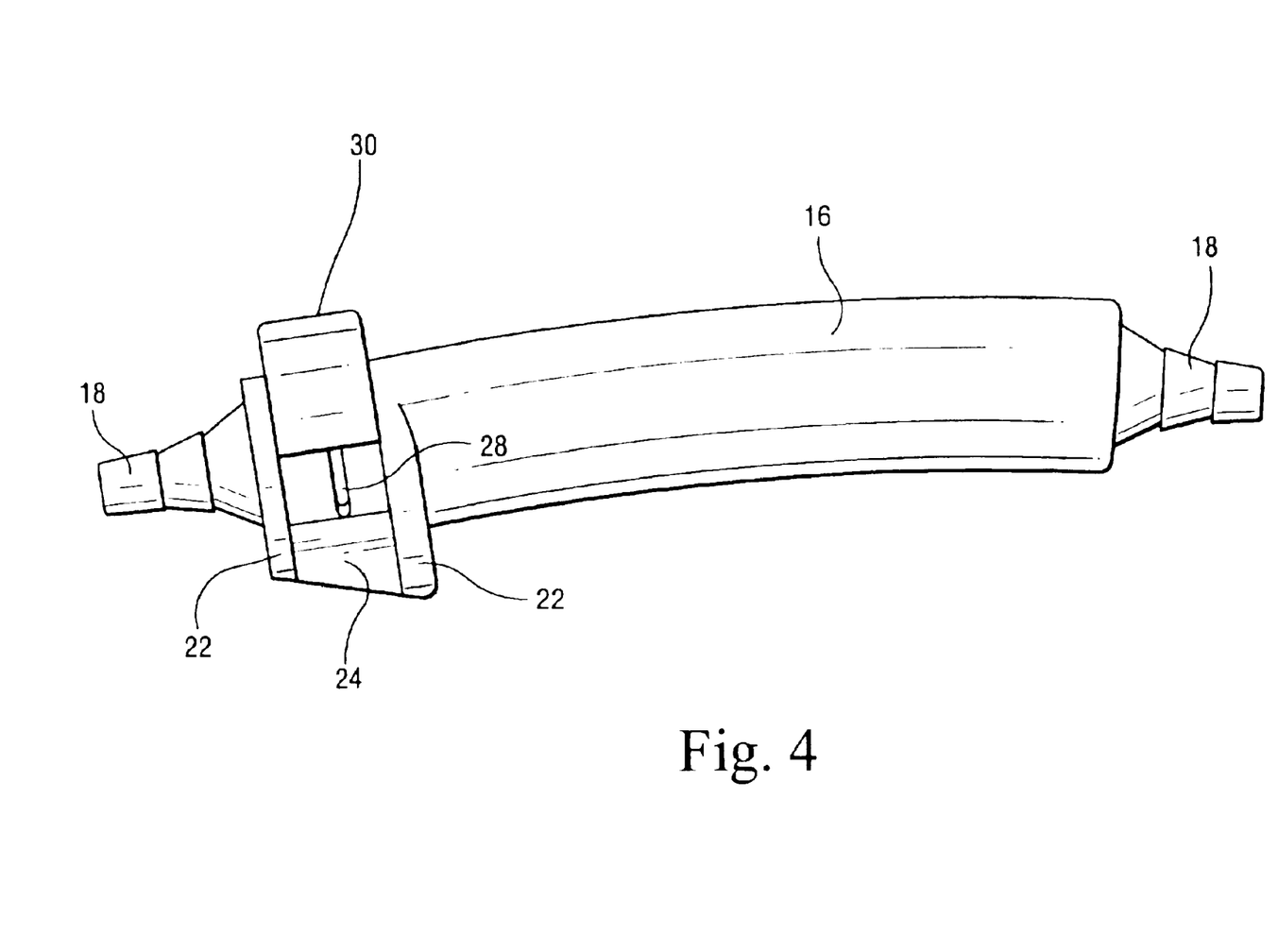
FIG. 4 is a perspective view of a further side portion of the suction regulator valve.
Figure 5:
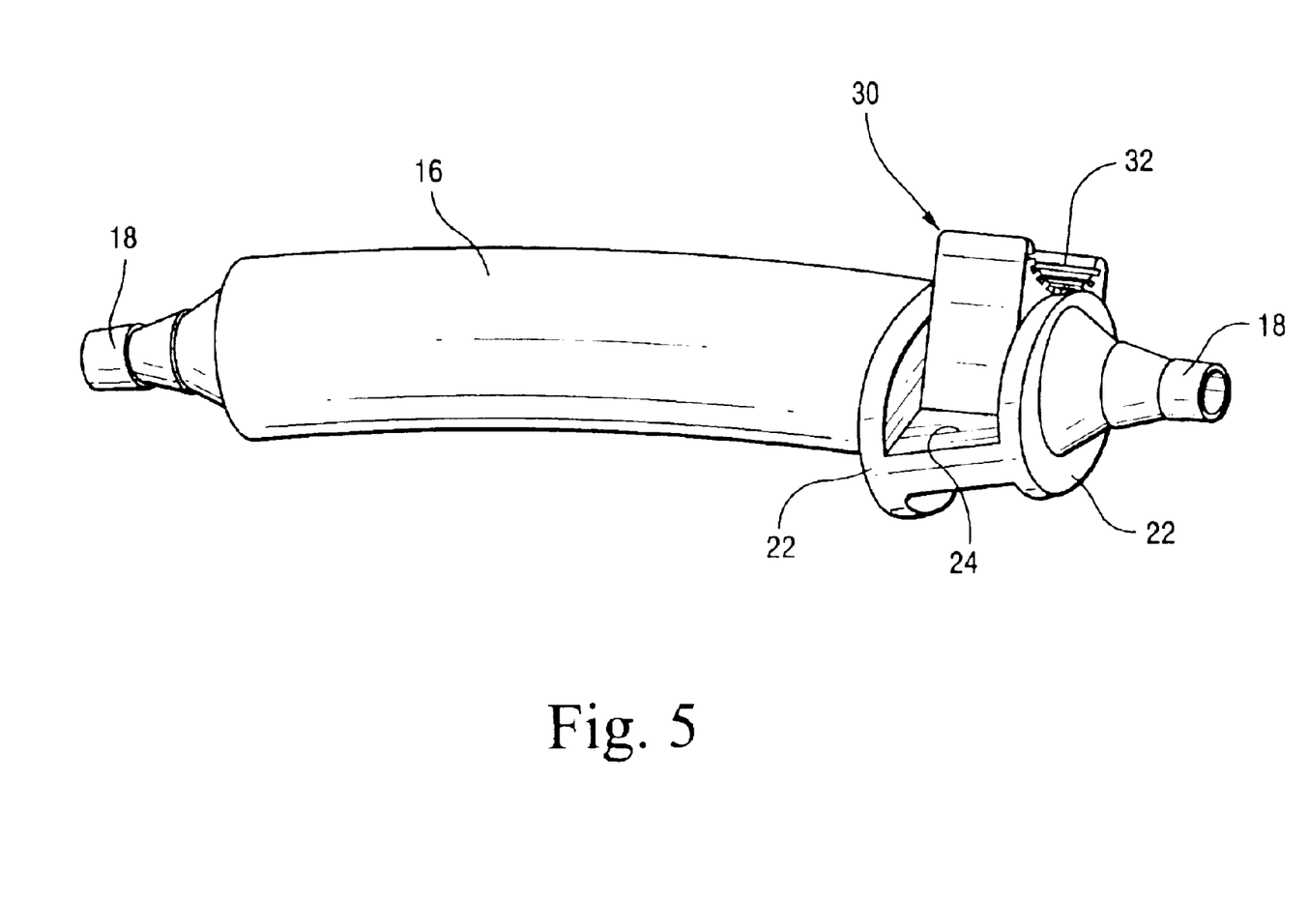
FIG. 5 is a perspective view of a still further side portion of the suction regulator valve.

A valve member 30 is rotatably or slidably mounted in any suitable manner on the outer surface 26 of the valve body 20 between the end walls 22 and is movable between the open position shown in FIGS. 1–6, wherein the opening 28 is uncovered, and a closed position (not shown) wherein it covers the opening 28. In the open position, one edge of the valve member 30 engages one side of the stop 24 (see FIG. 5), and in the closed position the other edge of the valve member 30 engages the opposite side of the stop 24. Preferably, the valve member 30 is provided with a knurled or grooved outer portion 32 that may be recessed as shown in FIGS. 2, 3 and 5, or not recessed as shown at 132 in FIG. 7, to facilitate the gripping and movement thereof by the thumb or other finger of the user, while being held in one hand, to control the position of the valve member 30 relative to the opening 28.

Figure 7:
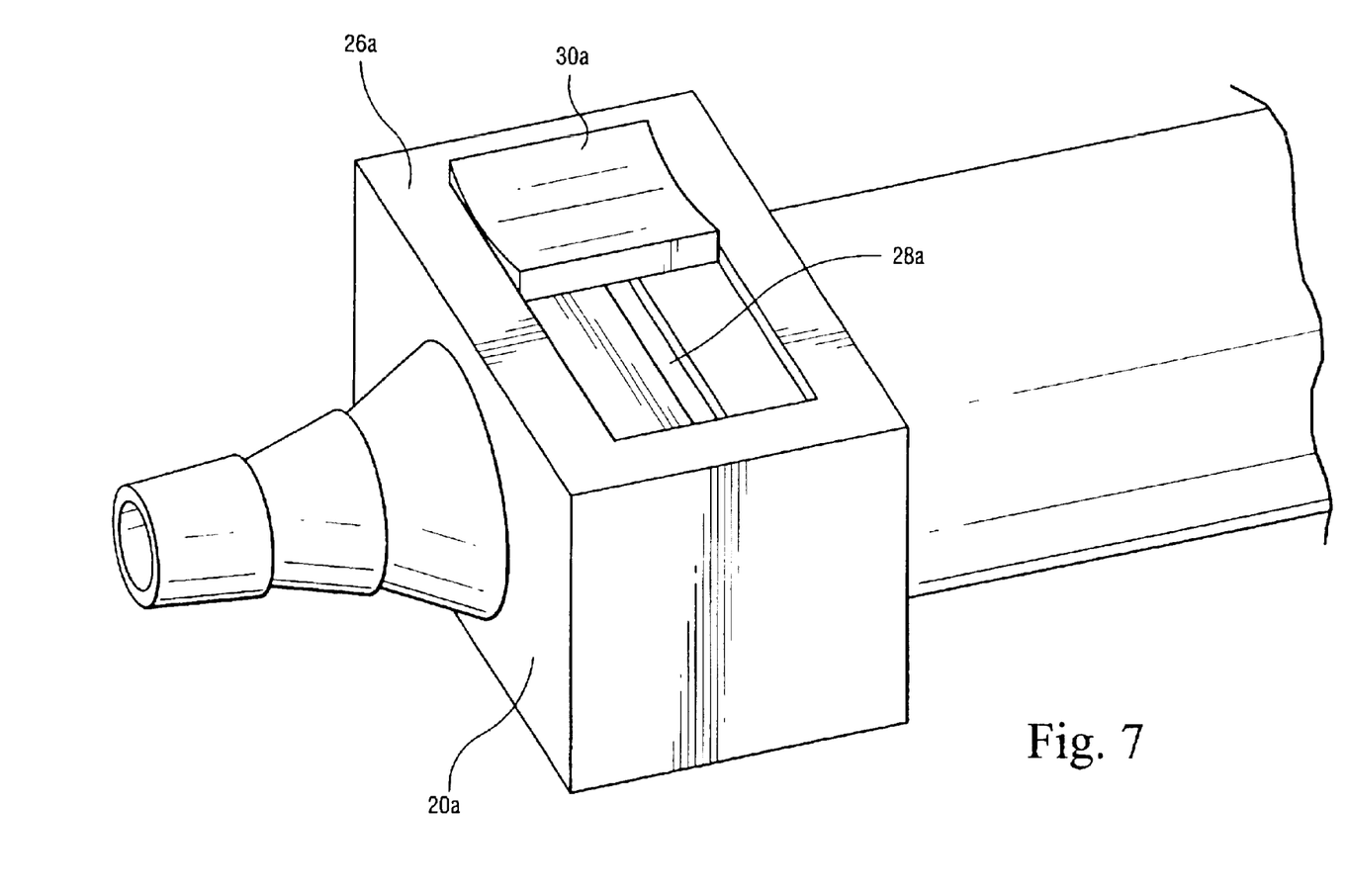
FIG. 7 is a perspective view of a further embodiment of the suction regulator valve having a valve body with a generally flat outer surface.

Within the scope of the present invention, the valve body 20a may be of any suitable cross section and may have a flat, planar outer surface 26a, as shown in FIG. 7 which may or may not be recessed. A transverse opening 28a is provided in the surface 26a and a valve member 30a is slidably mounted on the valve body surface 26a to open or close the opening 28a.

Figure 6:
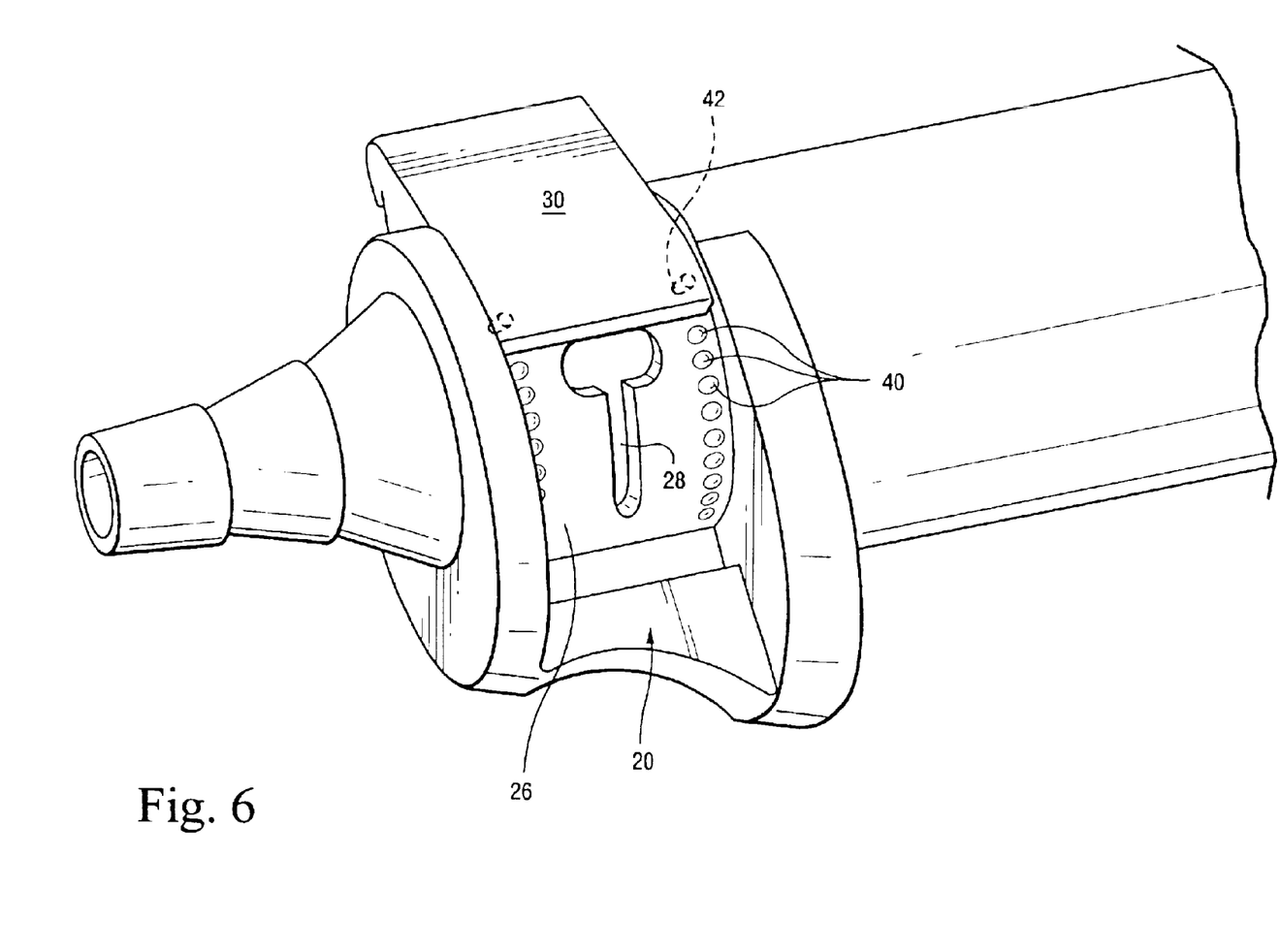
FIG. 6 is an enlarged perspective view of a portion of the suction regulator valve shown in FIG. 4.

The opening 28 may have a "keyhole" shape to facilitate the release of all suction when it is completely uncovered, as shown in FIGS. 1 and 6. Also, the opening 28 could be slightly oblique or off the transverse or circumferential axis, and could have any suitable shape other than the "keyhole" shape, in accordance with the principles of the present invention.

For applications where space is limited, the handle portion 16 of the valve body 12 could be omitted, as shown in FIG. 1a. Also, the handle portion 16 could be of any suitable size and shape. Similarly, the outer portion 32 of the valve member 30 may be of any suitable size and shape.

The valve member 30 and valve body 20 may be constructed in any suitable manner to provide for controlled, incremental movement of the valve member 30 relative to the valve body 20 and retention of the valve member in a desired position. As an illustrative example, 5 the recessed surface 26 of the valve body 20 may be provided with a plurality of circumferentially spaced indentations 40 on both sides of the slot 28, as shown in FIG. 6. The inner surface of the valve member 30 is provided with protrusions 42 that are positioned to be snap-fitted into the indentations 40 to provide for incremental movement of the valve member and its retention in a desired position.

Figure 8:
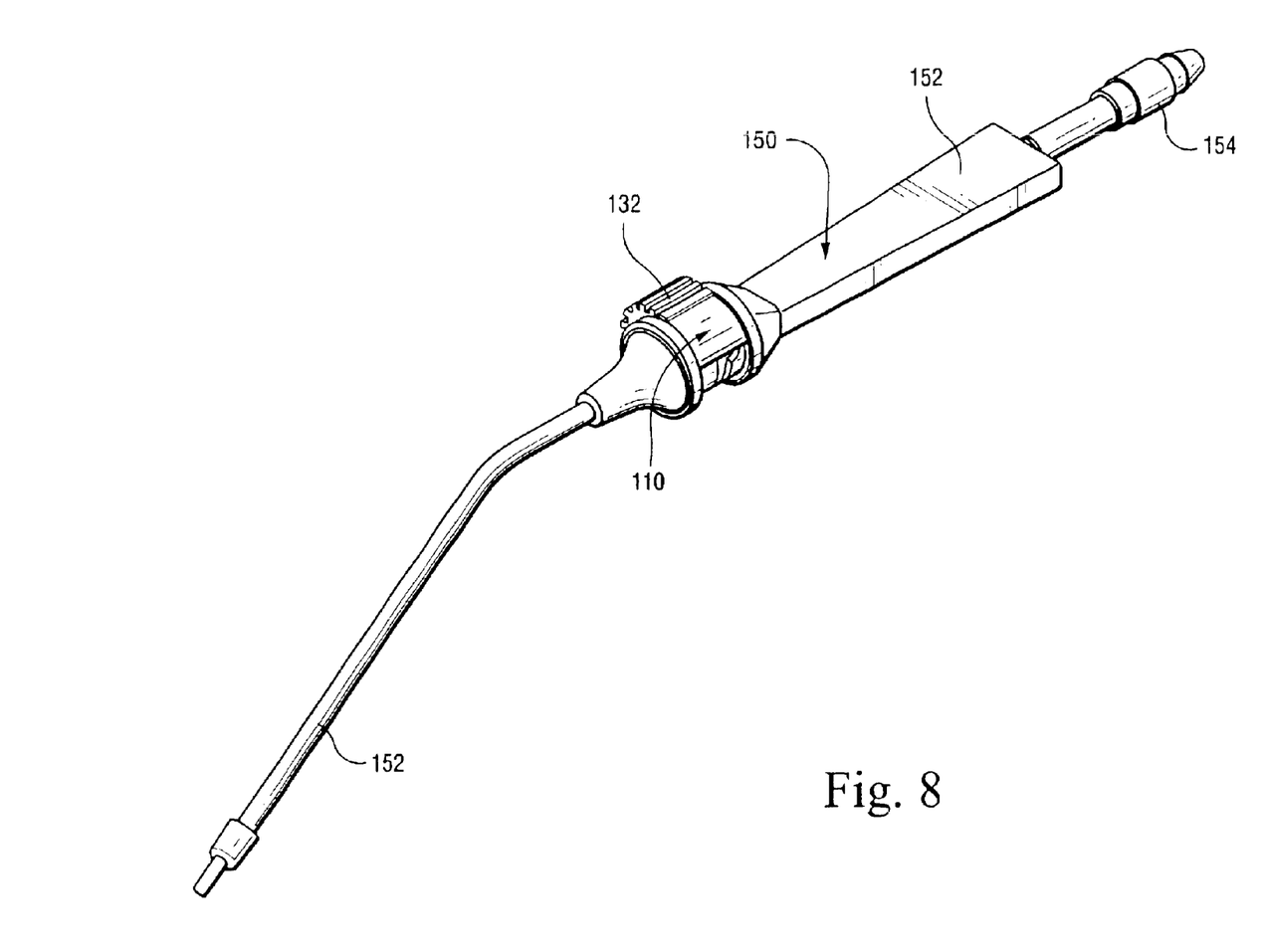
FIG. 8 is a perspective view of a second embodiment of the present invention wherein the suction regulator valve is constructed as an integral part of a suction wand or device.

FIG. 8 illustrates a second embodiment of the present invention wherein the suction regulator valve 110 of the present invention is constructed as part of a suction wand or device 150 comprising a suction catheter or tip portion 152 connected to one side of the valve 110, a hollow handle portion 154 connected to the other side of the valve 110, and a connector portion 156 connected to the outer end of the handle portion 154 for connection to a suction pump (not shown) or the like. The handle portion 154 may be omitted and the connector portion 156 connected directly to the valve 110.

Figure 9:
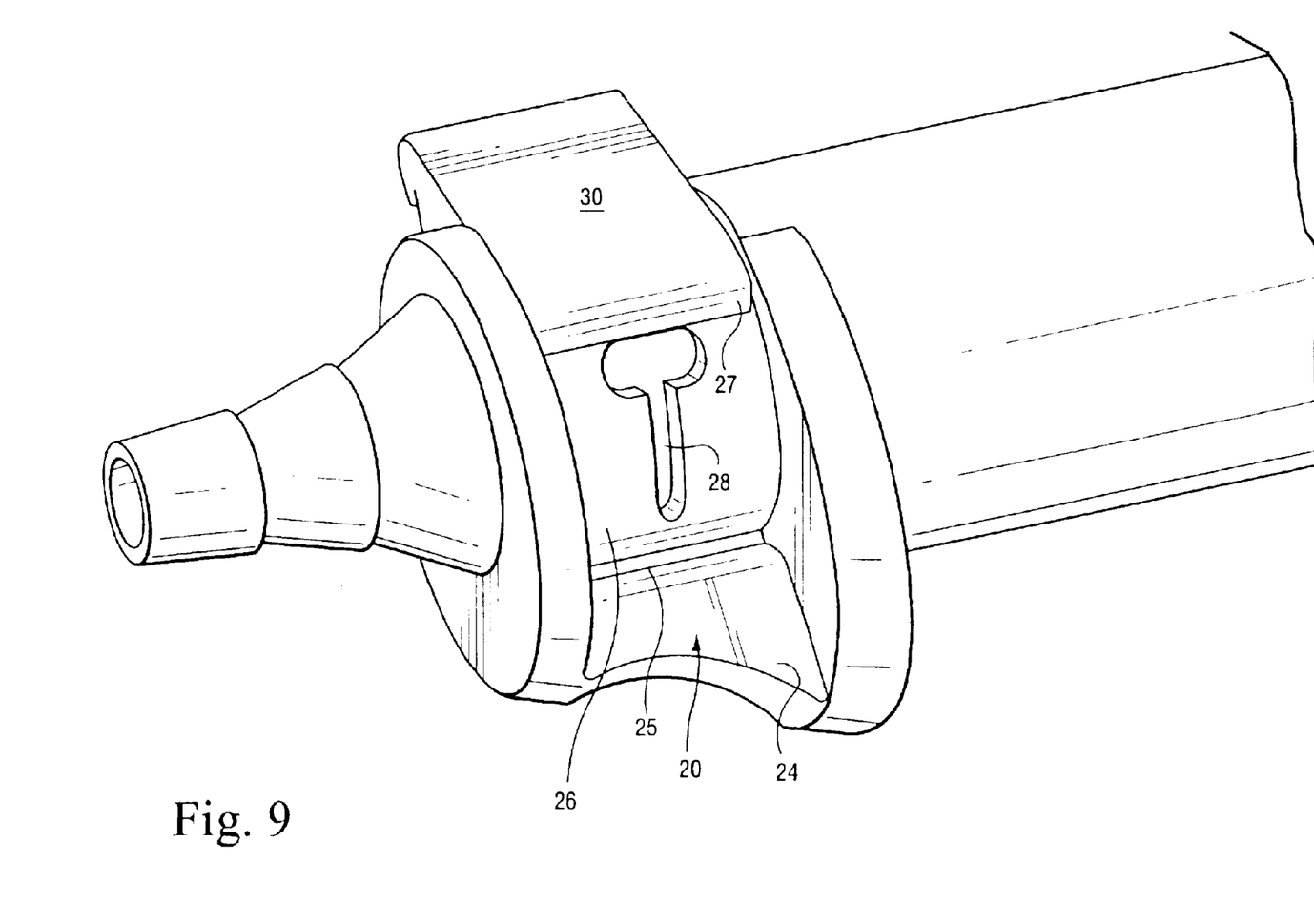
FIG. 9 is an enlarged perspective view similar to FIG. 6 showing a still further embodiment of the suction regulator.

The valve member 30 and valve body 20 may be constructed in any suitable manner to insure that they are in sealing engagement to prevent leakage through the opening 28 and loss of suction when the valve member 30 is in the closed position wherein it covers the opening 28. For example, the valve member 30 could be formed of a flexible and resilient material so that it would be drawn into sealing contact with the valve body 20 by the suction through the opening 28 when in the closed position. As an alternative, the portion of the stop 24 near the valve body surface 26 could be provided with a tapered recess as shown at 25 in FIG. 9, and the portion of the valve member 30 adjacent thereto when in the closed position could be provided with a complementary tapered end 27 that would be received in the recess 25 as the valve member was being moved to the closed position to urge it inwardly into tight sealing engagement with the adjacent outer surface 26 of the valve body 20.

Some of the advantages of the present suction regulator valve are as follows:

1. The generally transverse or circumferential orientation of the opening 28 allows the valve portion 14 to be of a small size or width to facilitate its incorporation in other surgical tools, such as a suction wand or the like;
2. The transverse or circumferential movement of the valve member 30, rather than axial or longitudinal movement thereof, helps to prevent its inadvertent movement if there is a pull on the suction tubing connected to it;
3. The valve member can be easily operated by either hand of the user and can be connected to suction tubing in any direction;
4. The valve member 30 can be easily moved by the thumb or other finger of a user, while the suction valve is held in one hand, to cover all, a portion of or none of the opening 28; and
5. The valve is simple in construction, easy and inexpensive to manufacture, reliable in operation and easy to install in a suction device.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A suction regulator valve adapted to be installed between a suction pump or other vacuum source and a suction tube or catheter, said valve comprising:
    a hollow valve body having an outer surface with a generally transverse opening therethrough, and
    a valve member slidably mounted on said valve body for generally transverse movement on said outer surface thereof, said valve member being movable between an open position wherein said opening is uncovered and a closed position wherein said valve member covers and closes said opening;
    wherein said valve body comprises a stop for limiting the opening and closing movement of said valve member.
2. The valve of claim 1 wherein said valve member is positioned for engagement by the thumb or other finger of a user to enable the movement of said valve member to cover or uncover all or a portion of said opening.
3. The valve of claim 1 wherein said valve body comprises a hollow handle portion connected thereto and positioned to enable the gripping thereof by one hand of a user and the engagement of said valve member by the thumb or other finger of the one hand of the user.
4. The valve of claim 3 wherein said valve body and said handle portion have connector members on the outer ends thereof for attachment to a suction tube, vacuum source or the like.
5. The valve of claim 3 wherein said handle portion is connected to one end of said valve body, and further comprising a suction member attached to the other end of said valve body.
6. The valve of claim 1 wherein said valve body comprises axially spaced end walls, and said stop comprises a wall extending generally longitudinally between said end walls.
7. The valve of claim 6 wherein said valve body is of generally cylindrical configuration, said valve member is of generally annular shape, and said opening is a generally circumferential slot.

8. The valve of claim 7 wherein said end walls are generally elliptical in shape.

9. The valve of claim 1 wherein said valve body and said valve member are constructed to enable the incremental movement of said valve member relative to said valve body and the retention of said valve member in a desired position.

10. The valve of claim 1 wherein said valve body is of generally cylindrical configuration, said valve member is of generally annular shape, and said opening is a generally circumferential slot.

11. The suction regulator valve of claim 1 wherein said valve member is in sealing engagement with the adjacent outer surface of said valve body when in said closed position.

12. A suction regulator valve adapted to be installed between a suction pump or other vacuum source and a suction tube or catheter, said valve comprising:

a hollow valve body having an outer surface with a generally transverse opening therethrough, and a valve member slidably mounted on said valve body for generally transverse movement on said outer surface thereof, said valve member being movable between an open position wherein said opening is uncovered and a closed position wherein said valve member covers and closes said opening;

said valve body comprising a stop for limiting the opening and closing movement of said valve member;

wherein said valve body comprises axially spaced end walls, and said stop comprises a wall extending generally longitudinally between said end walls; and said outer surface of said valve body is recessed between said end walls, and said valve member is slidable on said outer surface between said end walls.

13. The valve of claim 12 wherein said valve member is in slidable engagement with said end walls.

14. A suction regulator valve adapted to be installed between a suction pump or other vacuum source and a suction tube or catheter, said valve comprising:

a hollow valve body having an outer surface with a generally transverse opening therethrough, and a valve member slidably mounted on said valve body for generally transverse movement on said outer surface thereof, said valve member being movable between an open position wherein said opening is uncovered and a closed position wherein said valve member covers and closes said opening;

wherein said valve body and said valve member are constructed to enable the incremental movement of said valve member relative to said valve body and the retention of said valve member in a desired position; and wherein said valve body and said valve member are provided with transversely spaced indentations and complementary protrusions for removable engagement with said indentations.

15. A suction regulator valve adapted to be installed between a suction pump or other vacuum source and a suction tube or catheter, said valve comprising:

a hollow valve body having an outer surface with a generally transverse opening therethrough, and a valve member slidably mounted on said valve body for generally transverse movement on said outer surface thereof, said valve member being movable between an open position wherein said opening is uncovered and a closed position wherein said valve member covers and closes said opening;

wherein said valve member is in sealing engagement with the adjacent outer surface of said valve body when in said closed position;

wherein said valve member is formed of a flexible and resilient material to enable it to be drawn into sealing engagement with the adjacent outer surface of said valve body when in said closed position.

16. A suction regulator valve adapted to be installed between a suction pump or other vacuum source and a suction tube or catheter, said valve comprising:

a hollow valve body having an outer surface with a generally transverse opening therethrough, and a valve member slidably mounted on said valve body for generally transverse movement on said outer surface thereof, said valve member being movable between an open position wherein said opening is uncovered and a closed position wherein said valve member covers and closes said opening;

wherein said valve member is in sealing engagement with the adjacent outer surface of said valve body when in said closed position;

wherein said valve body comprises a stop for limiting the opening and closing movement of said valve member, and said stop has a recess near said outer surface of said valve body which is positioned to receive the adjacent end portion of said valve member as it is being moved to said closed position to urge it into sealing engagement with the adjacent outer surface of said valve body.

17. The suction regulator valve of claim 16 wherein said recess in said stop and said adjacent end portion of said valve body are tapered in a complementary manner.

* * * * *